(12) United States Patent
Graham

(10) Patent No.: US 6,390,987 B1
(45) Date of Patent: May 21, 2002

(54) METHOD AND APPARATUS FOR SEPARATING WATER AND GAS IN A GAS ANALYZER SYSTEM

(75) Inventor: James E. Graham, Pewaukee, WI (US)

(73) Assignee: Ge Marquette Medical Systems, Inc., Milwaukee, WI (US)

( * ) Notice: Subject to any disclaimer, the term of this patent is extended or adjusted under 35 U.S.C. 154(b) by 0 days.

(21) Appl. No.: 09/631,582

(22) Filed: Aug. 3, 2000

(51) Int. Cl.$^7$ .................................................. A61B 5/08
(52) U.S. Cl. ....................................... 600/529; 600/532
(58) Field of Search ................................. 600/529, 532; 73/23.3; 422/84

(56) References Cited

U.S. PATENT DOCUMENTS

| | | | | |
|---|---|---|---|---|
| 4,713,095 A | * | 12/1987 | Ricciardelli | .................. 55/189 |
| 4,717,403 A | * | 1/1988 | Choksi | ......................... 55/429 |
| 4,997,463 A | * | 3/1991 | Ricciardelli | .................. 55/165 |
| 5,131,387 A | | 7/1992 | French et al. | .......... 128/205.27 |
| 5,209,761 A | * | 5/1993 | Ivester et al. | .................. 95/271 |

* cited by examiner

Primary Examiner—Robert L. Nasser
Assistant Examiner—Patricia Mallari
(74) Attorney, Agent, or Firm—Foley & Lardner; Peter J. Vogel; Michael A. Della Penna

(57) ABSTRACT

A liquid and gas separator system is disclosed, the liquid and gas separator system includes an inlet that receives a first gas sample. The first gas sample at least partially includes liquid introduced from a patient in a gaseous or liquid form. The liquid and gas separator system also includes a first chamber coupled to the inlet and configured to receive the first gas sample. The first chamber includes a drain aperture. An outlet is coupled to the first chamber and is configured to receive a second gas sample from the first chamber. The second gas sample is derived from the first gas sample, that is the second gas sample includes less liquid than the first gas sample. The second chamber is substantially sealed around the first chamber. The first chamber receives a combined gas and liquid from the inlet and separates at least some of the liquid from the gas. The first chamber is configured to have liquid deposited at the bottom of the first chamber. The liquid deposited at the bottom of the first chamber is subsequently transferred to the second chamber through the drain aperture by a pumping action created by a pressure gradient in the inlet line. The pressure gradient is created by liquid water at least partially blocking the free flow of gas through the sample line inlet.

33 Claims, 2 Drawing Sheets

US 6,390,987 B1

METHOD AND APPARATUS FOR SEPARATING WATER AND GAS IN A GAS ANALYZER SYSTEM

FIELD OF THE INVENTION

The invention relates generally to systems for monitoring a medical patient's condition, and more particularly to monitoring systems including a water and gas separator system for removing liquid which has condensed from a patient's exhalation gases.

BACKGROUND OF THE INVENTION

During medical treatment of a patient, it may be desirable to monitor a patient's exhalation and, in some instances, to analyze the exhalation gas composition. Monitoring of exhalation gases, for example, may be used in analysis of apnea conditions or in the analysis of exhalation of a patient that is under anesthesia. Typically, a patient's exhalation is monitored by providing at least a portion of the patient's exhalation to a suitable sensor or analyzer.

Accurate analysis of gases in a patient's exhalation depends, in part upon the collection of the flow of exhalation gases without the introduction of factors that may distort results of the analysis. Introduction of contaminants into the flow, or other alteration of the exhalation gases in the monitoring system, may render analytical results that do not reflect the actual condition or near actual condition of the patient.

Because a patient's exhalation is usually relatively humid, condensed liquid must be removed before the gases reach the sensor. Liquid, such as water, may condense as exhalation gases flow from a patient to the gas analyzer or sensor. Therefore, two possible sources of moisture contamination exist, i.e., entrainment in exhalation and re-entrainment of prior condensation into a subsequent stream of exhalation. Condensation can result in inaccurate readings at the sensor or analyzer. Additionally, collected condensation can interrupt the smooth flow of exhalation to the sensor, another possible distortion of the sensor operation. Further still, sensing devices used in patient monitoring systems, such as an infrared spectrometer, are often delicate and can be uncalibrated by liquid entering the sensor system.

In order to remove liquid from the exhalation to prevent distortion of the gaseous composition of exhalation (gas waveform developed by the sensor or analyzer) and to protect the sensor or analyzer devices, it has been known to place a liquid and gas separator or a moisture trap between the patient and the sensing device to separate liquid and/or moisture from the exhalation gases before it enters the sensing device.

Some prior art liquid and gas separator and/or moisture trap designs utilize a porous hydrophilic material to separate water vapor from a flow of exhalation gases. While hydrophilic materials may effectively remove a quantity of condensed moisture from a flow of humid gas, their use in some prior liquid and gas separator and moisture trap designs have introduced other problems. For example, hydrophilic materials are porous and include voids. Such prior art liquid and gas separators and moisture trap designs, using hydrophilic materials, remove moisture from exhalation by allowing the exhalation to pass in proximity with or through the hydrophilic material. These arrangements can alter the gaseous composition of the exhalation being monitored by allowing gases held in the porous hydrophilic material to become re-entrained and mixed with flow of exhalation. More specifically, the re-entrainment or mixing may be in the form of previously exhaled gas or sampled gas which had been held in the voids and later released into a subsequent stream of exhaled air or sampled gas, thereby distorting the gas content of that subsequent stream. Thus, when the stream reaches the sensor, it is not an accurate representation of the patient's condition at that instant and therefore an erroneous gas waveform is produced by the sensing device or analyzer. The greater the volume of hydrophilic material exposed to the flow of exhalation, generally the greater volume of gas which can be stored therein and hence the greater volume of gas available to later contaminate the exhalation. Minimizing the volume of hydrophilic material used in some prior art designs can decrease the amount of such mixing, but can also undesirably decrease the capacity of the liquid and gas separator or moisture trap. Further, it is known in some prior art liquid and gas separator or moisture trap designs to utilize devices that are fully disposable or partially disposable. Utilizing fully disposable or partially disposable liquid and gas separator or moisture trap designs creates higher costs to consumers, such as patient's, hospitals, or health care facilities. These costs may be reduced by utilizing reusable moisture traps or liquid and gas separators.

Accordingly, there is a need for a liquid and gas separator for removing condensed moisture from a flow of exhalation without substantially altering the gaseous composition of the exhalation. Further, there is a need to provide a liquid and gas separator system such that the liquid and gas separator device is reusable. Further still, there is a need for a water separator system that has an expanded capacity to contain condensed moisture from a patient's exhalation thereby assuring that liquid will not pass through the liquid and gas separator and into the sensor. Yet further still, there is a need for a liquid and gas separator system that may be easily emptied, or cleaned during the course of a medical procedure.

SUMMARY OF THE INVENTION

An exemplary embodiment of the invention relates to a liquid and gas separator. The fluid and gas separator includes an inlet and an outlet. The fluid and gas separator also includes a first chamber coupled to the inlet. The first chamber has a drain aperture and a second chamber is substantially sealed around the first chamber. The first chamber receives a combined gas and liquid from the inlet, and separates at least some of the liquid from the gas. The liquid is deposited at the bottom of the first chamber. The liquid deposited at the bottom of the first chamber is subsequently transferred to the second chamber through the drain aperture.

Another exemplary embodiment of the invention relates to a gas analysis system utilized to separate liquid from a gas sample. The system includes a gas sample source providing a first gas sample. The first gas sample at least partially includes liquid introduced from the source in a gaseous or liquid form. The system also includes an inlet receiving the first gas sample. Further the system includes an outlet providing a second gas sample. The second gas sample being derived from the first gas sample. The second gas sample includes substantially no liquid. Further still, the system includes a gas analyzer coupled to the outlet and configured to analyze the content of the second gas sample. Yet further still, the system includes a first chamber coupled to the inlet. The first chamber has a drain aperture and a second chamber substantially sealed around the first chamber. The first chamber receives a combined gas and liquid from the inlet, and separates at least some of the liquid separates from the gas. The liquid is deposited at the bottom of the first chamber, and liquid deposited at the bottom of the first chamber is subsequently transferred to the second chamber through the drain aperture.

Still another exemplary embodiment of the invention relates to a liquid and gas separator system. The system includes an inlet receiving a first gas sample. The first gas sample at least partially includes liquid introduced from a patient in a gaseous or liquid form. The system also includes a first chamber coupled to the inlet and configured to receive the first gas sample. The first chamber has a drain aperture. Further, the system includes an outlet, coupled to the first chamber and configured to receive a second gas sample from the first chamber. The second gas sample being derived from the first gas sample. The second gas sample includes substantially no liquid. Further still, the system includes a second chamber substantially sealed around the first chamber. The first chamber receives a combined gas and liquid from the inlet, and separates at least some of the liquid from the gas. The first chamber is configured to have liquid deposited at the bottom of the first chamber, and liquid deposited at the bottom of the first chamber is subsequently transferred to the second chamber through the drain aperture.

Yet still another exemplary embodiment of the invention relates to a method of analyzing a gas sample. The method includes receiving a first gas sample into a first expansion chamber. The method also includes separating liquid from the first gas sample. Further, the method includes providing liquid from the first chamber to the second chamber through a drain aperture in the first chamber. Further still, the method includes providing a second gas sample from the first chamber to a gas analyzer.

BRIEF DESCRIPTION OF THE DRAWINGS

The invention will become more fully understood from the following detailed description, taken in conjunction with the accompanying drawings, wherein like reference numerals refer to like elements, in which.

DETAILED DESCRIPTION OF EXEMPLARY EMBODIMENTS

Figure 1:
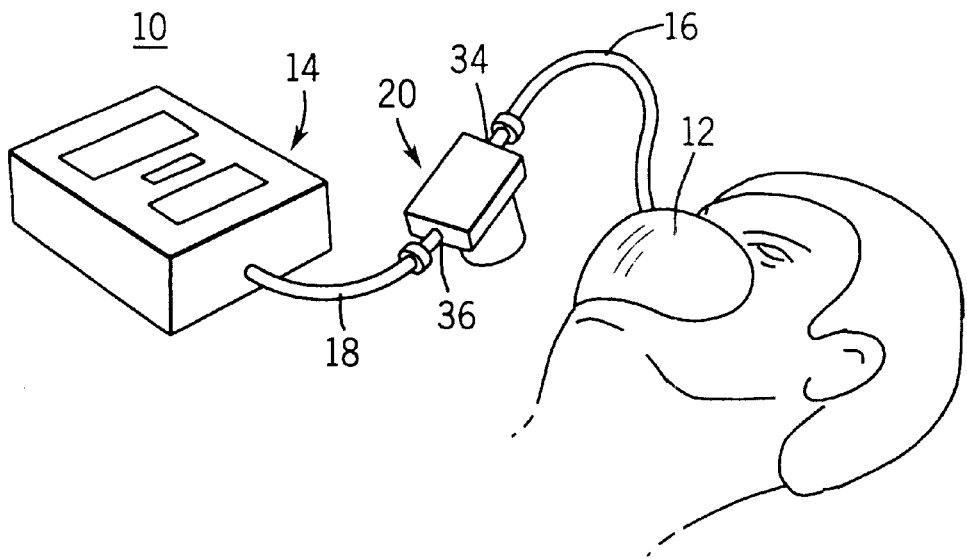
FIG. 1 is a perspective view of a patient monitoring system depicting a gas analyzer and a liquid and gas separator.

As illustrated in FIG. 1, a patient monitoring system 10 includes a device 12 for collecting a flow of a patient's exhalation gases. While the collection device 12 is shown in the form of a mask placed over a patient's nose and mouth, other standard collection devices may be used.

Monitoring system 10 also includes a sensing device or gas analyzer 14. While it is understood that various sensing devices may be successfully and advantageously used, it is contemplated that in the exemplary embodiment disclosed, sensing device 14 may be a conventional infrared spectrometer operable to analyze the gaseous composition of a patient's exhalation including, for example, carbon dioxide ($CO_2$) or anesthesia gas content. It is also contemplated that sensing device 14 include an apnea monitor (not shown) for detecting a complete stoppage of the flow of exhalation. Yet further still, it is contemplated that monitor 14 be a type of chemical analyzer as opposed to an electronic and optical analyzer.

A pair of conduits 16 and 18 communicate between collection device 12 and sensing device 14 to provide a flow path for exhalation. Conduits 16 and 18 may be standard conduits or cannulas. In an exemplary embodiment, the conduits are made of a conventional flexible clear plastic. In an exemplary embodiment, a liquid and gas separator 20 is connected between conduits 16 and 18 and between collection device 12 and sensing device 14. Conduit 16 connects device 12 to an inlet 34 to liquid and gas separator 20 and conduit 18 is coupled to an outlet 36 of liquid and gas separator 20 and to an inlet of gas analyzer 14. Liquid and gas separator 20 is provided to remove condensed liquid from the flow of exhalation to protect sensing device 14 from the introduction of liquid and insure the reliability of the sensor as a patient monitor.

Figure 2:
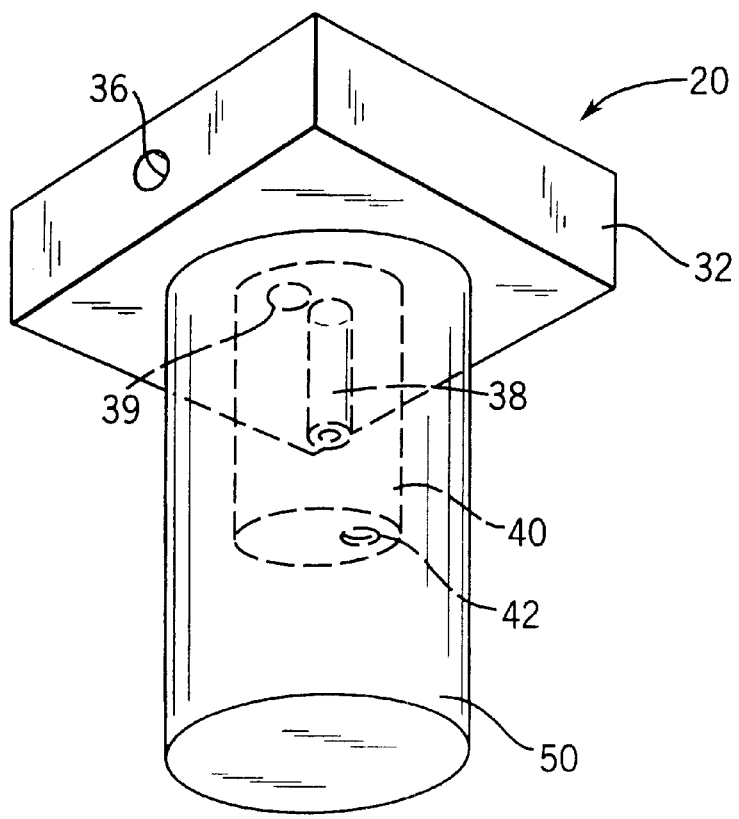
FIG. 2 is a perspective view of an exemplary embodiment of a liquid and gas separator.

It is preferable to have a liquid and gas separator that is low cost, has a reservoir that can be emptied by a user, the liquid and gas separator not requiring a separate vacuum system, and a system in which decrease in performance due to contamination or aging is minimized. Referring now to FIG. 2, a liquid and gas separator 20 accomplishes the aforementioned advantages by the use of gravity and the natural pressure gradient movement when water travels through a sample line into liquid and gas separator 20. As depicted, liquid and gas separator 20 includes a base 32 including a sample inlet 34 and a sample outlet 36 (see also FIGS. 1 and 3). Sample inlet 34 extends through base 32 and into a first chamber 40 via a chamber inlet 38. First chamber 40 is substantially sealed around chamber inlet 38 and chamber outlet 39. First chamber 40 further includes a drain aperture 42 fluidly connected with a second chamber 50. Second chamber 50 is substantially coupled to and sealed by base 32.

Figure 3:
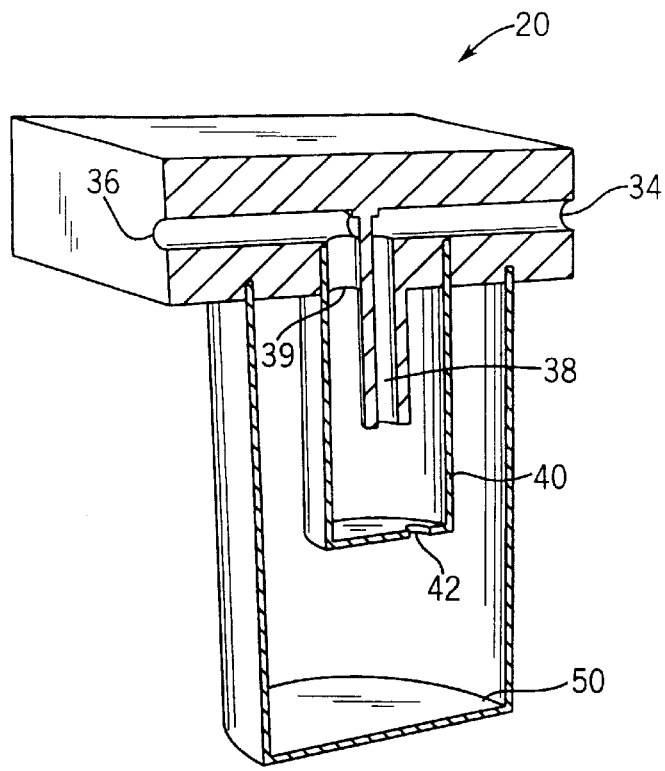
FIG. 3 is a cross sectional view of the liquid and gas separator of FIG. 2.

A first step in removing liquid (such as water) from a sampled gas without destroying the gas wave front may be to pass the gas and liquid through a shape (an expansion chamber, for example) that will slow the gas and liquid velocity down to allow gravity to take action on the liquid. Such a shape should also open to a volume that cannot support the liquid surface tension bridging across the internal walls, thus allowing the liquid to bead and fall to the bottom of the chamber. FIGS. 2 and 3 depict an exemplary embodiment of such a shape that is combined to perform this function. In operation, sample gas water vapor condenses on the internal wall of sample line 16 (see FIG. 1), the condensation building to an amount that collects, breaks loose and travels along the sample line wall. This collection of condensation causes an avalanche of liquid along the internal wall where more and more liquid is pulled into the bead of liquid and bridges the wall circumference. The liquid clings to the wall slowing the gas flow and soon causing a gas pressure drop across the liquid bead. A lower pressure is then created on the analyzer 14 side of separator 20 by a pump in analyzer 14 and a high pressure on the sampling of separator 20 side begins to propel the liquid droplet into the liquid and gas separator. To eliminate the change of liquid jumping from inlet 38 to outlet 39, first chamber inlet 38 is extended into first chamber 40. The low mass of the gas coming from inlet 38 can follow the shape of the walls of first chamber 40 and exit through outlet 39, but the liquid will be trapped in first chamber 40.

Thus, any liquid and gas entering from a patient and device 12 travels through line 16 into inlet 34 through inlet 38 to first chamber 40 where the condensed liquid separates from the gas. The gas continues into outlet 39 and through outlet 36 to conduit 18 and analyzer 14. First chamber 40 includes drain aperture 42 to prevent first chamber 40 from filling with liquid. Liquid from first chamber 40 exits chamber 40 through drain aperture 42 into sealed second chamber 50. It is important that second chamber 50 be a sealed chamber to preserve the proper pressure drop which encourages liquid from first chamber 40 into second chamber 50 while preventing gas to be exchanged between first chambers 40 and second chamber 50. In normal operation, liquid and gas separator 20 would have the same pressure in second chamber 50 as first chamber 40. Any gas exchange between first chamber 40 and second chamber 50 would be only from the diffusion of gas molecules through drain aperture 42, which would be slight and would cease once the first drop of liquid entered the cup and substantially blocked the hole, due to the liquid surface tension. The liquid surface tension across drain aperture 42 would not allow liquid to enter second chamber 50 if it were not for the pumping action of the droplet in the sample line, that is a droplet in line 16 or inlet 34 causes a pressure drop in chamber 40.

For example, the pressure at a pump in analyzer 14 may be 660 mmHg and the atmospheric pressure is 760 mmHg, a difference of 100 mmHg. If the sample line represents one unit of restriction out of the total restriction of 10 units, then it would have 10 percent of the drop or 10 mmHg. This makes the pressure where the sample line connects to gas analyzer 14 750 mmHg. When liquid enters sample line 16, the surface tension of the liquid clings to the walls of conduit 16, slowing the flow and causing restriction in the line to increase. If the increase were equal to 9 units of restriction, the pressure drop across the sample line would now be at the midpoint (9 to 9) or 50 percent of the total drop. In this example, that would be 50 mmHg. This gives a pressure where the sample line connects to analyzer 14 a pressure of 710 mmHg. If liquid and gas separator 20 were connected between sample line 16 and analyzer 14, analyzer 14 would see a pressure variance from 750 to 710 mmHg. This pressure variation can be used to pump the liquid and gas separator reservoir, with the help of gravity for direction, when liquid is in sample line 16, the pressure drops to 710 mmHg in first chamber 40. This causes air to pass through drain aperture 42 making the pressure in section chamber 50 drop to 710 mmHg. When new liquid enters the first chamber 40 and is separated, it collects at the bottom of first chamber 40. The liquid collected is now no longer in sample line 16 and the pressure in first chamber 40 returns to 750 mmHg. This forces liquid in first chamber 40 through drain aperture 42 and into second chamber 50, returning the pressure in second chamber 50 from 710 mmHg to 750 mmHg in the process. The next drop of liquid starts the entire process again.

It is important to note that a substantial performance advantage is obtained using the two-chamber liquid and gas separator system 20. Liquid and gas separator system 20 has the advantage of obtaining a final gas reading error that is substantially less than comparable systems. The advantage is obtained because of continuous sampled gas dilution in comparable systems which cause erroneous gas sample readings.

Figure 4:
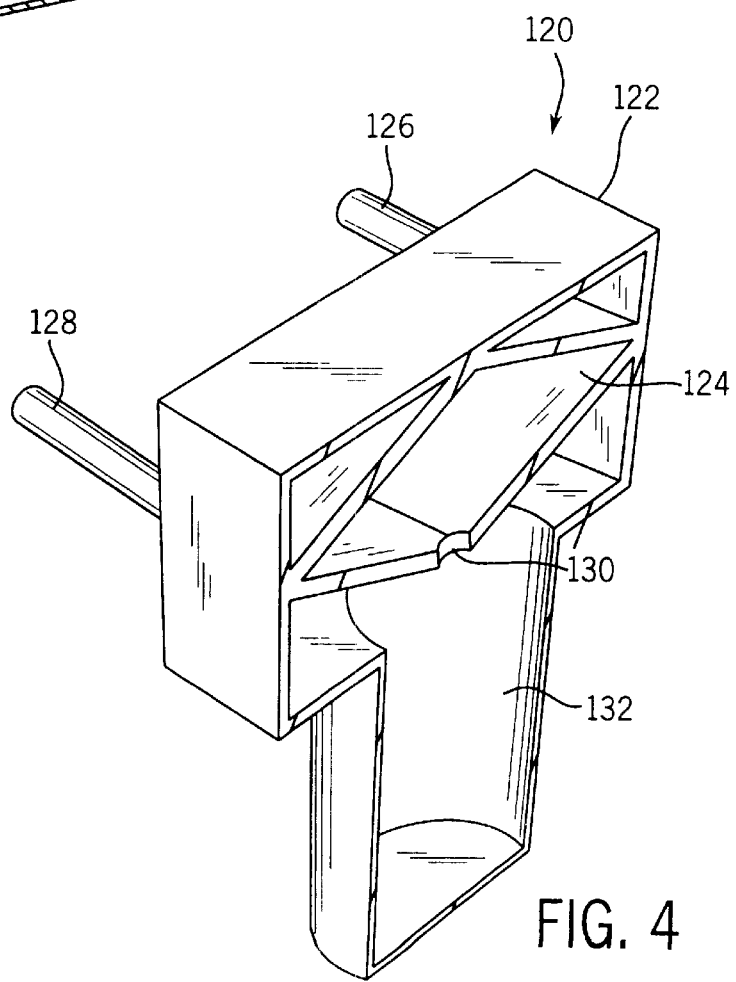
FIG. 4 is a cross sectional perspective view of an alternative embodiment of a liquid and gas separator.

Referring now to FIG. 4, an alternative embodiment of a liquid and gas separator device 120 is depicted. Liquid and gas separator device 120 includes a base 122, the base including a first chamber 24 with a sample gas inlet 26 and a sample gas outlet 28 fluidly connected to first chamber 24. First chamber 24 also includes an aperture 130 through which liquid separated from exhalation gas or other gas may flow into a second chamber 132. Second chamber 132 is substantially sealed to but removable from base 122. In operation, first chamber 124, which is preferably an at least partially conical shaped chamber, allows slowing of the liquid and gas velocity, coming from sample line 126, so that the liquid is separated from the gas by gravity and the liquid proceeds toward drain aperture 130. Further, the substantially conical shaped chamber provides a chamber in which the gas wave front may traverse the chamber without substantial turbulent back flow. In a particular embodiment, chamber 124 is shaped as two cones having their bases connected to each other, one cone expanding the gas from sample line 126 and then a second cone section compressing the gas wave front to proceed through sample line 128 to analyzer 14, the second cone restoring the sampled gas velocity while substantially maintaining gas wave front purity. Drain aperture 130 is configured similar to the drain aperture of the embodiment of FIG. 2 and the interaction with second chamber 132 works in substantially the same way as the embodiment depicted in FIGS. 2 and 3.

It should be noted that in the embodiments depicted in FIGS. 2, 3, and 4, second chamber 50 and 132 are removable from device 20 and 120 respectively so that second chambers 50 and 132 may be easily emptied and cleaned periodically. Further, it should be noted that devices 20 and 120 are designed to be reusable and do not require any disposable portions thereof.

While the exemplary embodiments refer to gas analyzers used in patients, the present invention may also be applied to gas analyzers used in a variety of different environments.

Further, while the exemplary embodiments refer to gas analyzers, the phrase is to be interpreted broadly. The embodiments may encompass those situations in which any type of electronic device is coupled to and in fluid communication with the outlet sample lines coming from devices 20 and 120.

Further still, those who have skill in the art will recognize that the present invention is applicable with many different hardware configurations and software architectures, embodied in the gas analysis devices, and organizations or processes utilized while utilizing the liquid and water separator systems 20 and 120.

While the detailed drawings, specific examples, and particular formulations given describe exemplary embodiments, they serve the purpose of illustration only. The materials and configurations shown and described may differ depending on the chosen performance characteristics and physical characteristics of the liquid and gas separator systems. For example, the size of the apertures, supply lines, and chambers used may vary. The systems shown and described are not limited to the precise details and conditions disclosed. Furthermore, other substitutions, modifications, changes, and omissions may be made in the design, operating conditions, and arrangement of the exemplary embodiments without departing from the scope of the invention as expressed in the appended claims.

What is claimed is:

1. A liquid and gas separator, comprising:
   an inlet;
   an outlet;
   a first chamber coupled to the inlet, the first chamber having a drain aperture; and
   a second chamber sealed around the first chamber, the only access to the second chamber, when sealed, being the drain aperture,
   wherein the first chamber receives a combined gas and liquid from the inlet, and separates at least some of the liquid from the gas, whereby the liquid is deposited at the bottom of the first chamber, and liquid deposited at the bottom of the first chamber is subsequently transferred to the second chamber through the drain aperture.

2. The liquid and gas separator of claim 1, wherein the inlet is coupled to a collection device.

3. The liquid and gas separator of claim 1, wherein the first chamber is substantially cylindrical.

4. The liquid and gas separator of claim 1, wherein the first chamber is at least partially substantially conical.

5. The liquid and gas separator of claim 1, wherein the second chamber is selectively removable.

6. The liquid and gas separator of claim 1, wherein the first inlet includes a tube extending partially into the first chamber.

7. The liquid and gas separator of claim 1, wherein the outlet is configured to be coupled to an electronic gas analyzer.

8. The liquid and gas separator of claim 1, wherein transfer of liquid to the second chamber through the drain aperture is at least partially caused by a pumping action.

9. A liquid and gas separator, comprising:

an inlet;

an outlet;

a first chamber coupled to the inlet, the first chamber having a drain aperture; and a second chamber sealed around the first chamber, wherein the first chamber receives a combined gas and liquid from the inlet, and separates at least some of the liquid from the gas, whereby the liquid is deposited at the bottom of the first chamber, and liquid deposited at the bottom of the first chamber is subsequently transferred to the second chamber through the drain aperture transfer of liquid to the second chamber through the drain aperture is at least partially caused by a pumping action, and the pumping action is caused by liquid at least partially blocking the free flow of gas through the inlet thereby creating a pressure gradient.

10. A gas analysis system utilized to separate liquid from a gas sample, comprising:

a gas sample source providing a first gas sample, the first gas sample at least partially including liquid introduced from the source in a gaseous or liquid form;

an inlet receiving the first gas sample;

an outlet providing a second gas sample, the second gas sample being derived from the first gas sample, the second gas sample including substantially no liquid;

a gas analyzer coupled to the outlet and configured to analyze the content of the second gas sample;

a first chamber coupled to the inlet, the first chamber having a drain aperture; and a second chamber sealed around the first chamber, the second chamber, when sealed, having exactly one aperture leading into the second chamber, the exactly one aperture being the drain aperture, wherein the first chamber receives a combined gas and liquid from the inlet, and separates at least some of the liquid separates from the gas, whereby the liquid is deposited at the bottom of the first chamber, and liquid deposited at the bottom of the first chamber is subsequently transferred to the second chamber through the drain aperture.

11. The gas analysis system of claim 10, wherein the inlet is coupled to a collection device.

12. The gas analysis system of claim 10, wherein the first chamber is substantially cylindrical.

13. The gas analysis system of claim 10, wherein the first chamber is at least partially substantially conical.

14. The gas analysis system of claim 10, wherein the second chamber is selectively removable.

15. The gas analysis system of claim 10, wherein the first inlet includes a tube extending partially into the first chamber.

16. The gas analysis system of claim 10, wherein transfer of liquid to the second chamber through the drain aperture is at least partially caused by a pumping action.

17. A gas analysis system utilized to separate liquid from a gas sample, comprising:

a gas sample source providing a first gas sample, the first gas sample at least partially including liquid introduced from the source in a gaseous or liquid form;

an inlet receiving the first gas sample;

an outlet providing a second gas sample, the second gas sample being derived from the first gas sample, the second gas sample including substantially no liquid;

a gas analyzer coupled to the outlet and configured to analyze the content of the second gas sample;

a first chamber coupled to the inlet, the first chamber having a drain aperture wherein transfer of liquid to the second chamber through the drain aperture is at least partially caused by a pumping action, and a second chamber sealed around the first chamber, wherein the first chamber receives a combined gas and liquid from the inlet, and separates at least some of the liquid separates from the gas, whereby the liquid is deposited at the bottom of the first chamber, and liquid deposited at the bottom of the first chamber is subsequently transferred to the second chamber through the drain aperture transfer of liquid to the second chamber through the drain aperture is at least partially caused by a pumping action, and the pumping action is caused by liquid at least partially blocking the free flow of gas through the inlet thereby creating a pressure gradient.

18. A liquid and gas separator system, comprising:

an inlet receiving a first gas sample, the first gas sample at least partially including liquid introduced from a patient in a gaseous or liquid form;

a first chamber coupled to the inlet and configured to receive the first gas sample, the first chamber having a drain aperture;

an outlet, coupled to the first chamber and configured to receive a second gas sample from the first chamber, the second gas sample being derived from the first gas sample, the second gas sample including substantially no liquid; and a second chamber sealed around the first chamber, the only access to the second chamber, when sealed, being the drain aperture, wherein the first chamber receives a combined gas and liquid from the inlet, and separates at least some of the liquid from the gas, whereby the first chamber is configured to have liquid deposited at the bottom of the first chamber, and liquid deposited at the bottom of the first chamber is subsequently transferred to the second chamber through the drain aperture.

19. The liquid and gas separator system of claim 18, wherein the inlet is coupled to a collection device.

20. The liquid and gas separator system of claim 18, wherein the first chamber is substantially cylindrical.

21. The liquid and gas separator system of claim 18, wherein the first chamber is at least partially substantially conical.

22. The liquid and gas separator system of claim 18, wherein the second chamber is selectively removable.

23. The liquid and gas separator system of claim 18, wherein the first inlet includes a tube extending partially into the first chamber.

24. The liquid and gas separator system of claim 18, wherein the outlet is configured to be coupled to an electronic gas analyzer.

25. The liquid and gas separator system of claim 18, wherein transfer of liquid to the second chamber through the drain aperture is at least partially caused by a pumping action.

26. A liquid and gas separator system, comprising:

an inlet receiving a first gas sample, the first gas sample at least partially including liquid introduced from a patient in a gaseous or liquid form;

a first chamber coupled to the inlet and configured to receive the first gas sample, the first chamber having a drain aperture;

an outlet, coupled to the first chamber and configured to receive a second gas sample from the first chamber, the second gas sample being derived from the first gas sample, the second gas sample including substantially no liquid; and a second chamber sealed around the first chamber, wherein the first chamber receives a combined gas and liquid from the inlet, and separates at least some of the liquid from the gas, whereby the first chamber is configured to have liquid deposited at the bottom of the first chamber, and liquid deposited at the bottom of the first chamber is subsequently transferred to the second chamber through the drain aperture transfer of liquid to the second chamber through the drain aperture is at least partially caused by a pumping action, and the pumping action is caused by liquid at least partially blocking the free flow of gas through the inlet thereby creating a pressure gradient.

27. A method of analyzing a gas sample, comprising:

receiving a first gas sample into a first expansion chamber;

separating liquid from the first gas sample;

providing liquid from the first expansion chamber to a second chamber through a drain aperture in the first chamber; and providing a second gas sample from the first chamber to a gas analyzer, wherein the only access to the second chamber is the drain aperture, when the second chamber is sealed to the first chamber.

28. The method of claim 27, wherein the first gas sample is received from a patient.

29. The method of claim 27, wherein the gas analyzer is a carbon dioxide analyzer.

30. The method of claim 27, further comprising:

condensing liquid from a gas sample in an inlet sample line.

31. The method of claim 30, further comprising:

creating a pressure gradient in the inlet sample line.

32. The method of claim 31, further comprising:

creating a pumping action caused by the pressure gradient.

33. The method of claim 32, further comprising:

pumping liquid from the first expansion chamber to the second expansion chamber through the drain aperture.

* * * * *

UNITED STATES PATENT AND TRADEMARK OFFICE
CERTIFICATE OF CORRECTION

PATENT NO.    : 6,390,987 B1
DATED         : May 21, 2002
INVENTOR(S)   : Graham It is certified that error appears in the above-identified patent and that said Letters Patent is hereby corrected as shown below:

<u>Title page,</u>
Item [73], Assignee, please delete "Ge" and replace it with -- GE --.

<u>Column 7,</u>
Delete lines 43-45.
Line 46, delete "an inlet receiving the first gas sample" and replace it with -- an inlet, adaptable to receive a first gas sample at least partially including liquid introduced from a gas sample source in a gaseous or liquid form --.

Signed and Sealed this

Twenty-fourth Day of December, 2002

JAMES E. ROGAN
*Director of the United States Patent and Trademark Office*